United States Patent [19]
Fletcher

[11] Patent Number: 5,382,249
[45] Date of Patent: Jan. 17, 1995

[54] ADJUSTABLE SURGICAL BLADE

[75] Inventor: Henry H. Fletcher, Folsom, Calif.

[73] Assignee: Synvasive Technology, Inc., Rancho Cordova, Calif.

[21] Appl. No.: 149,605

[22] Filed: Nov. 8, 1993

Related U.S. Application Data

[63] Continuation-in-part of Ser. No. 707,903, May 30, 1991, abandoned.

[51] Int. Cl.⁶ .................... A61B 17/00; A61B 17/32
[52] U.S. Cl. .................................... 606/79; 606/82; 606/176; 606/178
[58] Field of Search ................ 606/79, 82, 86–88, 606/175, 176, 177, 178; 30/166.3; 83/698, 700

[56] References Cited

U.S. PATENT DOCUMENTS

| | | |
|---|---|---|
| 2,455,655 | 12/1948 | Carroll . |
| 2,795,247 | 6/1957 | Topolinski . |
| 3,901,117 | 8/1975 | Hoffman .................. 83/698 |
| 3,905,105 | 9/1975 | Tuke ........................ 30/393 |
| 3,943,934 | 3/1976 | Bent ........................ 606/178 |
| 4,012,978 | 3/1977 | de Lanauze ............. 83/698 |
| 4,069,824 | 1/1978 | Weinstock ............... 128/317 |
| 4,386,609 | 6/1983 | Mongeon ................. 606/178 |
| 4,513,742 | 4/1985 | Arnegger ................. 606/178 |
| 4,584,999 | 4/1986 | Arnegger ................. 606/178 |
| 4,594,781 | 6/1986 | Hoffman .................. 83/698 |
| 5,263,972 | 11/1993 | Evans ...................... 606/176 |

Primary Examiner—Michael A. Brown
Attorney, Agent, or Firm—Raymond B. Cranfill

[57] ABSTRACT

A cutting saw blade for use with an oscillatory power tool used in surgical bone cutting procedures including a blade having a distal end provided with teeth whose tips are oriented in a substantially linear row so that the terminus of all teeth lie in a solitary plane. Other tooth profiles assist in the cutting phenomena. The cutting blade has several spaced-apart pairs of notches disposed in the blade edges. Each pair of notches is adapted to cooperate with a pair of pins disposed on the oscillatory power tool to firmly retain the cutting blade to the saw. By providing the cutting blade with several sets of notches, the cutting blade is adjustable, in that it can be retained within the oscillatory power tool at different lengths. It has been found that such an adjustable cutting blade, having teeth oriented in a solitary plane, does not lose efficiency as the length of the blade is changed.

20 Claims, 4 Drawing Sheets

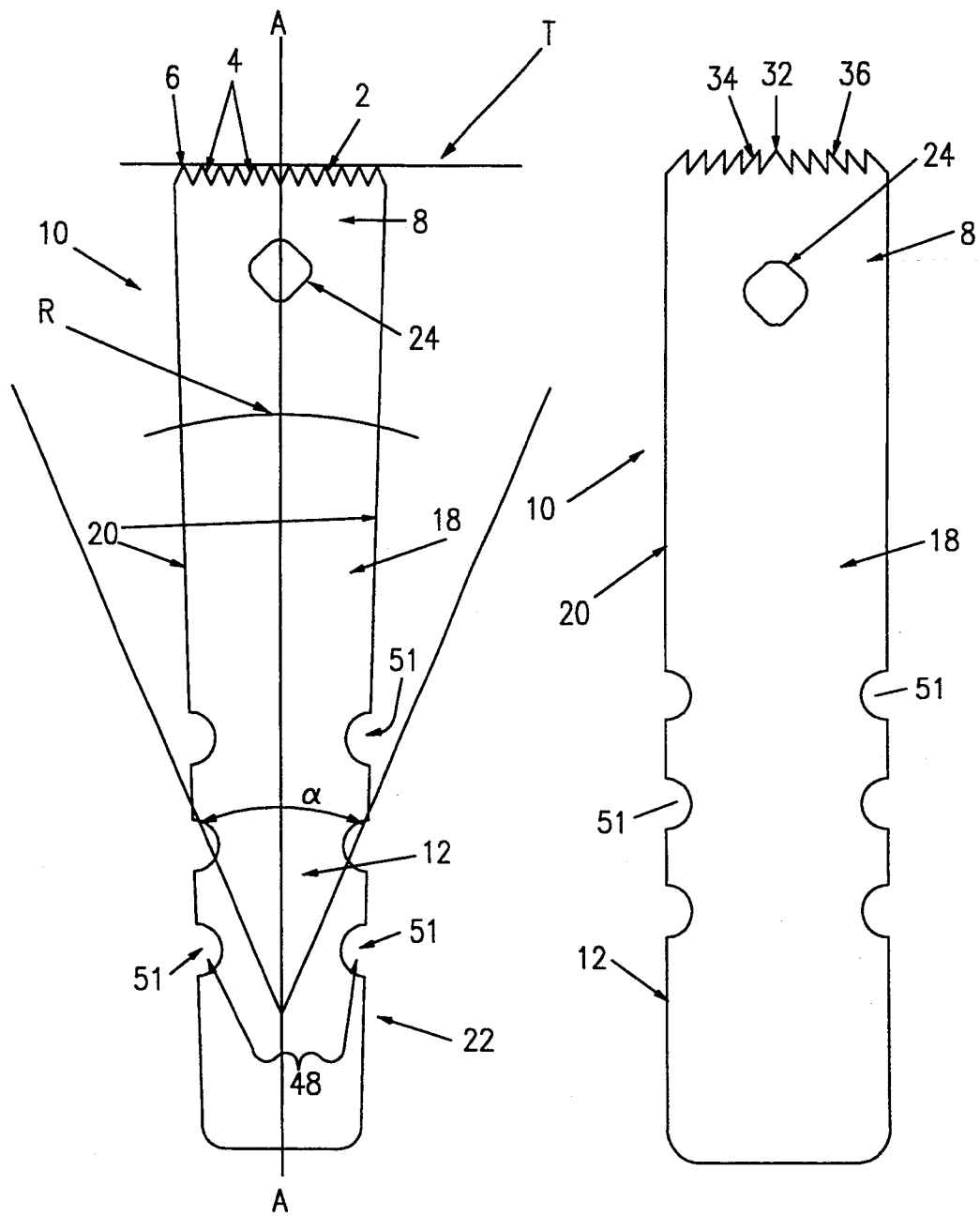

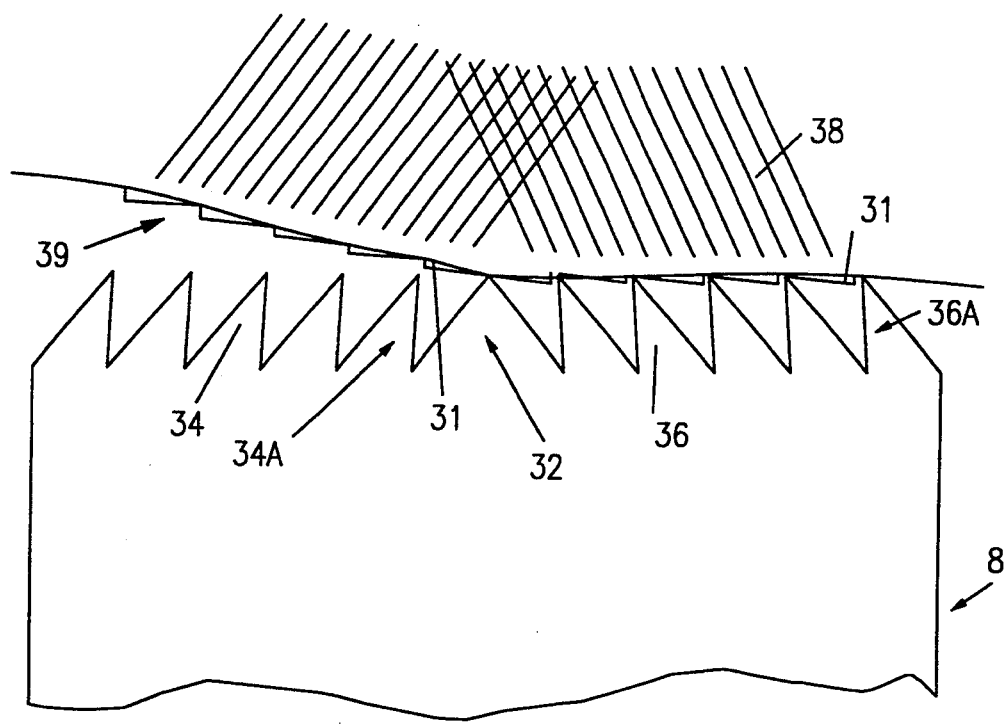
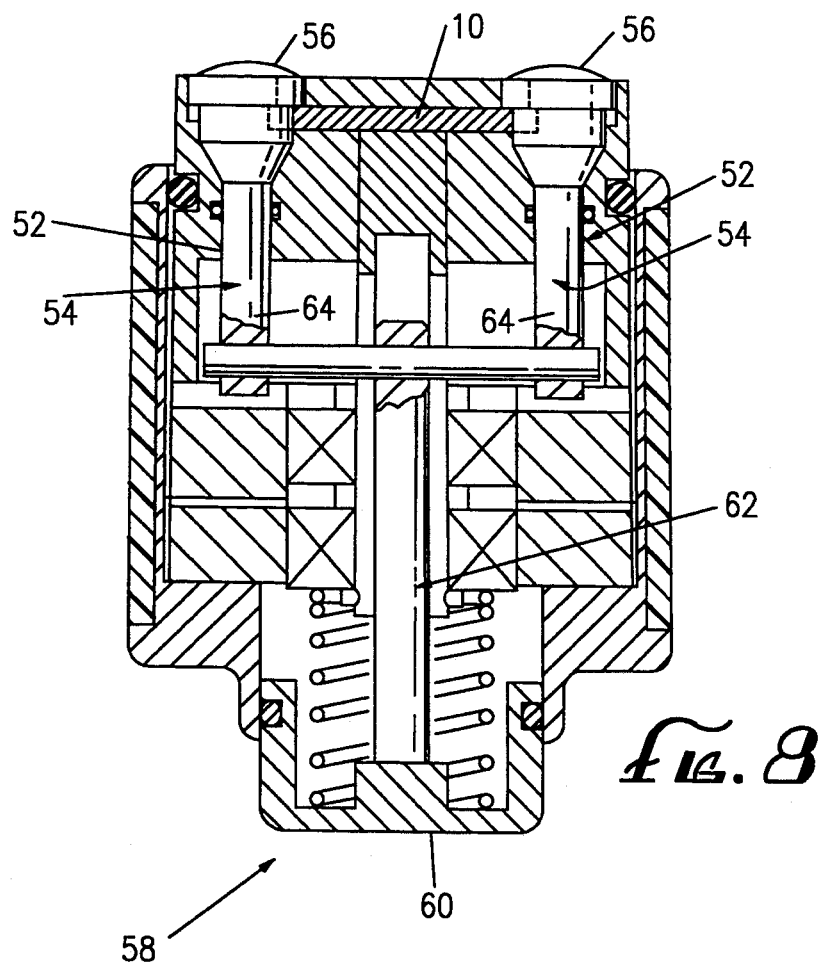

ADJUSTABLE SURGICAL BLADE

RELATED APPLICATION

This is a continuation-in-part of U.S. patent application Ser. No. 07/707,903, filed May 30, 1991, now abandoned. This application incorporates by this reference the entirety of U.S. patent application Ser. No. 07/707,903 as if set forth fully herein.

FIELD OF THE INVENTION

The following invention relates generally to instrumentalities for cutting bone during surgery. More particularly, the instant invention is directed to a saw blade adapted to be operatively coupled to an oscillatory (or sagittal) surgical power tool which pivots (or oscillates) the cutting blade back and forth about a small arc.

BACKGROUND OF THE INVENTION

One of the most vexing problems that surgeons face when using surgical bone saws is the tendency of the saw to "kick"; i.e., to become caught upon the bone being cut by the point of the saw tooth. Another form of kicking occurs where the kerf has the same contour as the blade which is due to the fact that the cutting surface (i.e., teeth) lies on the same radius as the radius of tool rotation. In this scenario, all teeth grab nearly at the same time. This causes the saw apparatus to rotate about that point, transmitting a rotational force back through the saw and to the surgeon. This kicking or grabbing that occurs causes a loss of accuracy in the cut from the sudden, unpredictable movements of the saw and induces increased fatigue by the surgeon because of the greater tension that the surgeon must maintain in his hands and arms in anticipation of receiving this kicking or grabbing motion.

Another problem noted in existing blades involves the tendency of the saw to initially wander rather than to form a kerf. One reason for this involves the nature of oscillatory cutter blades. The handle portion of the saw remains stable because it is near the surgeon's control and remote from the cutting. However, a blade (having a proximal end mounted into the oscillatory power tool) moves at a distal end that scribes an arc of a circle. Most surgical cutting saw blades have teeth on the distal extremity which are also oriented in an arc of constant radius. Especially when that arc has a geometrical center which coincides with the center of oscillatory motion, the bone to be penetrated is normally initially addressed by only one active cutting tooth in the series of teeth that resides on the arc, and as the blade completes its outward motion many teeth come into contact simultaneously. With several teeth contacting the bone, there is a greater tendency of the saw blade to kick and wander. The effect is even more pronounced when the blade's center of the arc of its teeth is between the oscillatory center of the power tool and the blade's distal end.

Another problem involves the non-aggressive nature of prior art blades. Even when more than one tooth contacts the bone, it is primarily due to the manipulation of the blade by the surgeon. The effect is that adjacent teeth do not effect progressive cutting and therefore make binding and kick back more likely.

Moreover, once the kerf has been formed, teeth doing the work in penetrating the bone, several other problems attend the cutting process. For one thing, substantially all the saw's teeth traverse along the entire extent, the cutting action is not as aggressive as it could be since the effect is an abrading one rather than chipping. Those teeth reside within the kerf for a longer period of time and tend to naturally generate more heat than had they been allowed outside the kerf. In addition, not having the teeth exit the working surface periodically tends to leave the chips of bone that have been abraded by the teeth to remain between the teeth. Lack of efficient chip removal is recognized as one cause of excessive heat generation. In surgical situations, such unwanted heat generation is undesirable because of thermal necrosis which damages bone structure adjacent to the cut.

In our previously-filed U.S. patent application Ser. No. 07/707,903, we proposed a surgical blade to overcome the foregoing problems. Unlike prior art cutting blades, the cutting blade proposed in the patent application Ser. No. 07/707,903 has teeth substantially on a tangent which is perpendicular to the longitudinal axis of the cutting blade. It has been found that such a cutting blade minimizes "kick," minimizes the initial tendency of the blade to wander, and minimizes heat build-up within the kerf.

It has now been discovered that an additional advantage of the cutting blade disclosed in the patent application Ser. No. 07/707,903 is that its cutting efficiency is not diminished by changing the length of the blade. This is contrasted with prior art cutting blades having teeth disposed on an arc. Such prior art blades are only efficient when the radius of the arc along which the teeth are disposed is the same as the distance between the teeth and the oscillating connection to the saw. The practical consequence of this fact is that a surgical hospital has to maintain an inventory of several different prior art cutting blades of any one particular style to accommodate its staff surgeons who prefer cutting blades of different lengths.

As noted above, however, the cutting efficiency of the blade disclosed in the patent application Ser. No. 07/707,903 is not effected by changes in the length of the blade. Accordingly, if the cutting blade of the patent application Ser. No. 07/707,903 could be modified to be adjustably attachable to a surgical saw at various lengths, a surgical hospital need retain only one particular style cutting blade in inventory.

Accordingly, there is a need for a surgical cutting blade which can be adjustably installed within a surgical saw so that the cutting blade can be used at various lengths without diminishing its cutting efficiency. There is also a need for a surgical saw and blade combination in which the cutting blade is adjustable in length without diminishing the cutting efficiency of the combination.

SUMMARY OF THE INVENTION

The present invention satisfies these needs. The invention is an oscillatory cutting blade, and a combination of the cutting blade and a surgical saw, useful for the surgical penetration of bone. The combination comprises an oscillatory power saw having a blade retention device and a cutting blade attached to the oscillatory cutting saw. The cutting blade has a central cutting blade shank with a longitudinal axis. The distal end of the cutting blade has a plurality of cutting teeth disposed substantially on a tangent perpendicular to the longitudinal axis of the cutting blade shank. The cutting blade also has a proximal end comprising a plurality of spaced-apart attachment elements, each of the attachment elements being capable of cooperating with the blade retention device so as to firmly attach the blade to the oscillatory cutting saw. The attachment elements are designed so that, when any one of the attachment elements is used to attach the cutting blade to the oscillatory cutting saw, the distance between the cutting teeth and the blade retention device is different than the distance between the cutting teeth and the blade retention device when the cutting blade is attached to the oscillatory cutting saw using a different attachment element.

The blade retention device can be a pair of spaced-apart parallel pins, each having a head and a shank. For embodiments having such a blade retention device, the attachment elements can be pairs of notches disposed on opposite sides of the cutting blade shank. The pins are shaped and dimensioned so that, when the shank of the blade is slipped between the pins, the heads of the pins cooperate with the pairs of notches to firmly retain the blade to the saw. In a preferred embodiment, the shanks of the pins have a smaller diameter than the heads, so that, when the pin heads are elevated above the cutting blade shank, the cutting blade is not firmly retained to the saw.

The cutting teeth on the blade can be a variety of shapes. In a typical embodiment, the teeth are substantially shaped as isosceles triangles. In a preferred embodiment, the teeth are substantially shaped as right triangles with the "hypotenuse" of each tooth facing either away from the center of the blade or towards the center of the blade.

DESCRIPTION OF THE DRAWINGS

These and other features, aspects and advantages of the present invention will become better understood with reference to the following description, appended claims and accompanying drawings where:

FIG. 1 is a top plan view of the apparatus according to the present invention in one form;

FIG. 2 is a top plan view of a second embodiment similar to FIG. 1;

FIG. 5 shows the blade of the present invention having progressed partially through a cut;

FIG. 8 is a detail cut away view of the combination of FIG. 6 taken along line 8—8.

DESCRIPTION OF PREFERRED EMBODIMENTS

Figure 3:
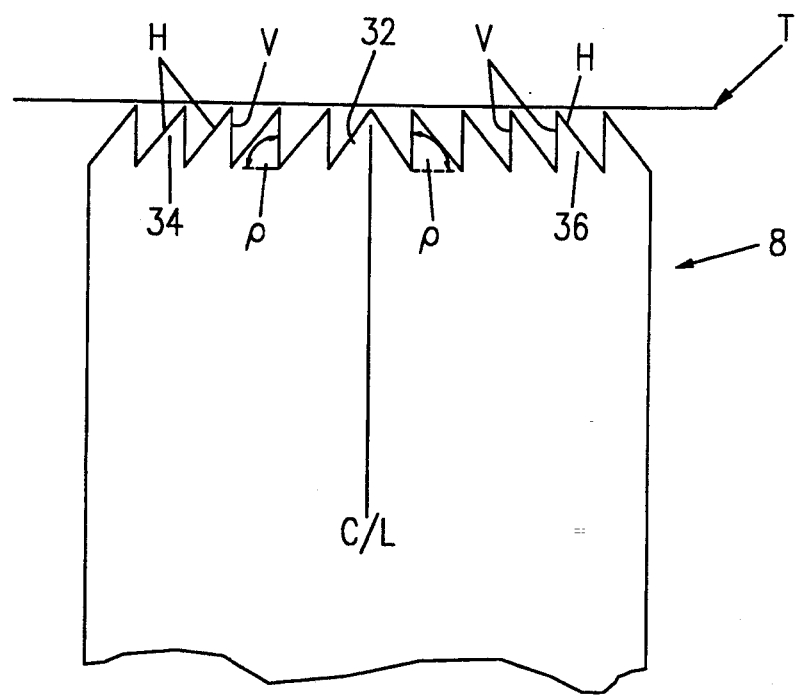
FIG. 3 is a close up detail of certain structure associated with the FIG. 2 embodiment.

Considering the drawings, wherein like reference numerals denote to like parts throughout the various drawing figures, a saw blade 10 includes a distal end 8 upon which a plurality of cutting teeth 2 are positioned and a proximal end 12 which is adapted to coact with and attach to an oscillatory (or sagittal) surgical power saw 14. Typically, an oscillating power tool swings through an arc a of 2° to 8° and at speeds ranging from 10,000 cycles per minute to 30,000 cycles per minute.

The blade 10 includes a shank 18 interposed between the proximal end 12 and the distal end 8. The shank 18 has a longitudinal axis A. In general, the shank 18 is formed from substantially flat stock material having side edges 20. The shank 18 can be tapered, as shown in FIG. 1, so that the blade 10 narrows as it goes from the distal end 8 to the proximal end 12. Alternatively, the side edges 20 can be parallel, as shown in FIG. 2.

In a typical embodiment, the overall length of the cutting blade 10 is between about 6 cm and about 18 cm. The width of the cutting blade 10 is between about 1 cm and about 4 cm, and the thickness of the cutting blade 10 is between 0.6 mm and about 2 mm.

In the embodiment shown in FIG. 1, the distal end 8 of the blade 10 includes a diamond shaped cutout 24 having radiused apices at the corners of the diamond. The diamond shaped cutout 24 is oriented such that two of the four radiused apices are coincident with the longitudinal axis A of the shank 18. In addition to providing a lighter blade 10, the diamond shaped cutout 24 tends to assist in tooth profiling during fabrication.

As mentioned, the distal end 8 of the saw blade 10 includes a plurality of teeth 2 disposed on the extremity of the distal end 8. Each of the teeth 2 is formed from two sides 4, which coalesce to form the tooth 2. The point of coalescence is defined as tip 6. The number of cutting teeth 2 on the blade 10 is not critical. In a typical embodiment, the number of cutting teeth 2 on the blade 10 is between about 6 and about 16 teeth.

Attention is directed to the embodiment of the invention shown in FIG. 1. Each of the teeth 2 are formed as isosceles triangles having all tips 6 located on a line T which is tangential to the oscillatory rotation R shown in FIG. 1. Thus, the tips 6 all are terminating on the tangent line T which exists at right angles to the longitudinal axis A of the cutting blade 10. This is measured when the blade is at an angle which is one-half its maximum arc swing.

FIG. 2 which shows a preferred variant of that which is shown in FIG. 1. Tooth details for FIG. 2 are shown in FIG. 3. As shown in FIG. 2, the blade 10 is generally characterized as one which is "reverse opposed"; i.e., having a plurality of teeth 2 which are inwardly directed. Stated in other words, when a centerline CL is drawn to bisect the teeth 2 into two sets, those teeth 2 which are to one side of the centerline CL face those teeth 2 on the other side.

As illustrated in FIG. 3, certain details of the tooth configuration shown in FIG. 2 can also now be better appreciated. One central tooth 32 has a tip 6 coincident with the center line CL. Thus, the central tooth 32 forms a substantially isosceles triangle similar to the teeth 2 shown in FIG. 1. Moreover, the center line CL serves as a line of demarcation between the left lateral side of the distal end 8 and the right lateral side of the distal end 8. As shown, the left lateral side includes a plurality of inwardly (i.e., towards central tooth 32) canted teeth 34. Conversely, the right lateral teeth 36 are also centrally canted toward the central isosceles tooth 32. Both of the left lateral teeth 34 and right lateral teeth 36 are formed substantially as right triangles with the right angle denoted by p. Actually p is slightly greater than 90° to provide a positive tooth rake when cutting.

The hypotenuse leg h of each triangle is outboard with respect to its vertical leg v. Recall that if p is greater than 90°, v may actually slope towards the center, providing positive rake. In this manner, the teeth 34 and 36 on opposite sides of the central tooth 32 "oppose" each other when cutting. The active cutting tip 6 is the end of the vertical leg v where it contacts leg h. The central tooth 32 is optional. Note that the teeth 2 in the embodiment illustrated in FIG. 3 also terminate along a tangent line T which is at right angles to the centerline CL.

FIG. 5 illustrates the tooth pattern of FIGS. 2 and 3 in the process of cutting a bone 38. FIG. 5 shows the cut after progress has been made in the cut. The cut has been exaggerated to explain the effect. As shown in FIG. 5, the kerf 39 is actually V-shaped about central tooth 32. As the right side teeth 36 cut, the left side teeth 34 are cooling and cleaning. As shown, the last tooth 36a has just finished cutting. The tooth labelled 34a is now about to make a cut. In effect each tooth 34 progressively takes a small cut 31 on each oscillatory stroke from the center then laterally outward. This can be viewed as "progressive staircasing" with the stairs (cuts 31) being removed one at a time. Stated alternatively, FIG. 5 shows a blade 10 just finishing in an advanced stroke of oscillation where the staircase of material on the left side of the center tooth 32 has already been removed (in an earlier stroke). Tooth 36 has stopped its leftward or inward motion and a progressive staircase looking kerf has been formed. As can be envisioned, when the left side teeth 34 are working, the right side teeth 36 are cooling and being cleaned of chips. The V-shaped kerf 39 is formed in practice.

Figure 4:
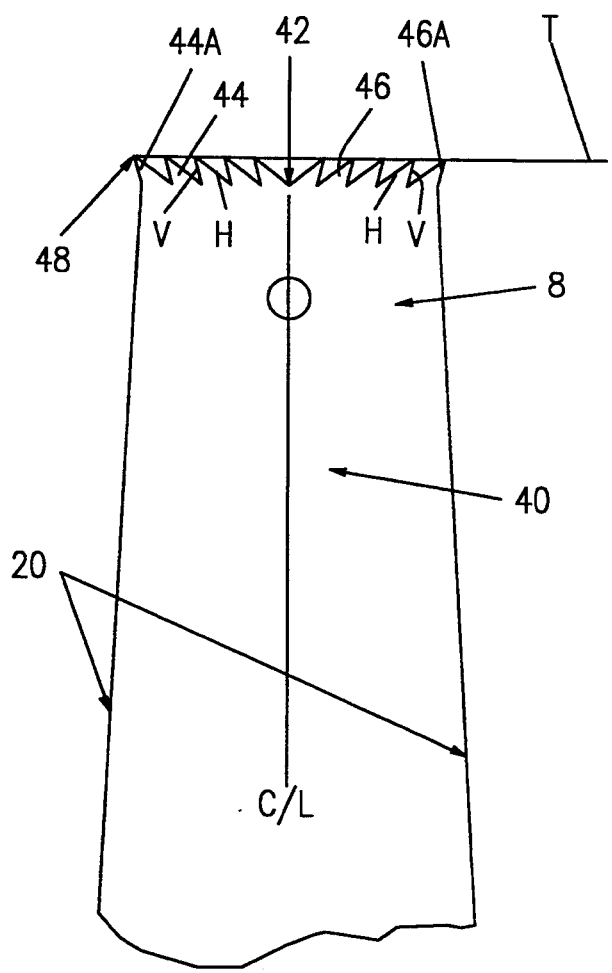
FIG. 4 shows a third embodiment with just the cutting head shown, similar to FIG. 3.

The distal end 8 of the embodiment illustrated in FIG. 4 bears some differences which need to be addressed. The cutting blade 10 is distinguished from the embodiment illustrated in FIGS. 1 and 2 by including a plurality of outwardly opposed teeth 12. More specifically, the centerline CL of the embodiment illustrated in FIG. 4 serves as an area of demarcation between the left side teeth 44 and the right side teeth 46. In the distal end 8 of the embodiment illustrated in FIG. 4, the centerline CL, when bisecting the teeth 2 between the left side teeth 44 and the right side teeth 46, passes through a central isosceles void 42 (i.e., the absence of a central tooth). The teeth 44 are similar to teeth 34 and 36 in the embodiments illustrated in FIGS. 2 and 3. However, the hypotenuse leg h of these triangles has been transposed 180° so that this leg h now faces the central isosceles void 42 and the vertical leg v is canted slightly to the "outside"; i.e., away from the central isosceles void 42, providing a negative rake. Using this structure, it is possible to appreciate that the teeth 2, according to this version, work opposite from those shown in FIG. 2. However, all teeth 2 in the embodiment illustrated in FIG. 4 are substantially "flat-top" configured as are the teeth 2 illustrated in FIG. 2; i.e., the tips 6 stop at the tangent T to the longitudinal axis A as in the first versions. Note the projection 48 of the outboard teeth 44a and 46b which extends beyond the side edges 20. The aggressive cutting pattern provided by teeth 44a and 46a has excellent stability in cutting and chip clearing properties analogous to the embodiment illustrated in FIG. 5 but opposite therefrom.

The proximal end 12 of the cutting blade 10 has a plurality of spaced-apart attachment elements 48, each of which is capable of cooperating with a blade retention device 50 on the oscillatory cutting saw 14 so as to firmly attach the blade 10 to the saw 14. The attachment elements 48 are disposed and operatively adapted on the cutting blade 10 so that, when the blade 10 is attached to the cutting saw 14 using any one attachment element 48, the distance between the blade retention device 50 of the cutting saw 10 and the cutting teeth 2 of the blade 10 is different from the distance between the blade retention device 50 and the cutting teeth 2 when the blade 10 is attached to the cutting saw 14 using a different attachment element 48.

Figure 6:
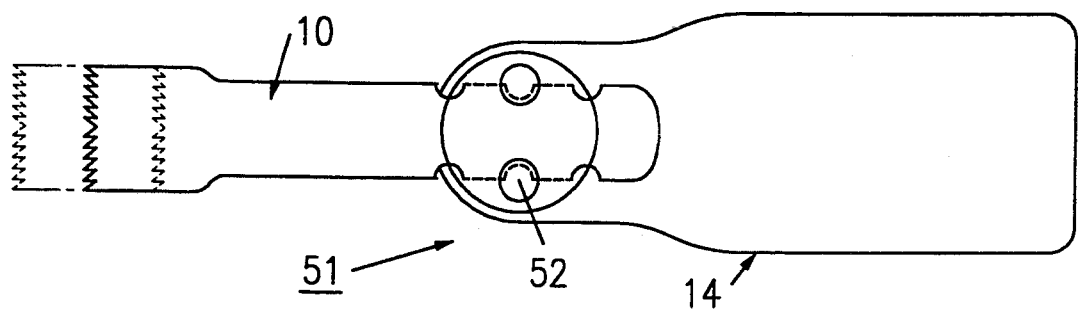
FIG. 6 is a top view of a combination surgical saw and cutting blade having features of the invention.
Figure 7:
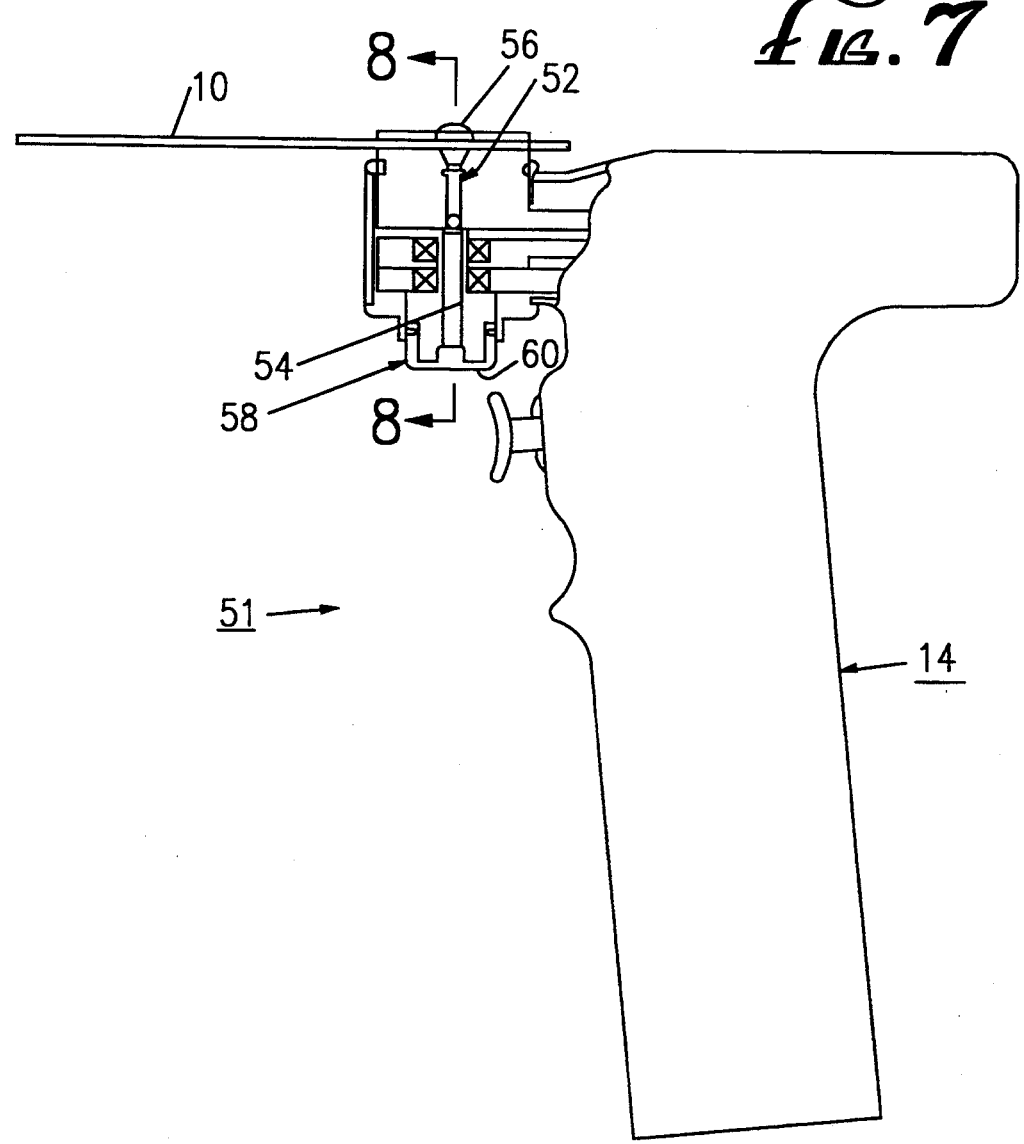
FIG. 7 is a side view in partial cutaway of the combination of FIG. 6.

As shown in the drawings, the attachment elements 48 can be a plurality of spaced-apart pairs of notches 51 defined within the edges of the cutting blade 10. These notches 51 are shaped and dimensioned to cooperate with a pair of pins 52 in the blade retention device 50 of the cutting saw 14 so that the blade 10 is firmly attached to the cutting saw 14 by the pins 52. FIGS. 6–8 illustrate this embodiment. The distance between the pairs of opposed notches is not critical. In a typical embodiment, the pairs of opposed notches are spaced-apart by between about 1 cm and about 5 cm.

In FIGS. 6–8, the combination of the cutting blade 10 and the saw (oscillatory cutting tool) 52 is shown. The blade retention device 50 of the saw 14 is adapted to oscillate as driven by an electric motor within the saw 14 (not shown). The blade retention device 50 comprises a pair of parallel pins 52. Each pin 52 has a pin shank 54 and a bulbous pin head 56. The distance between the two pin shanks 54 is greater than the distance between each pair of notches 51 so that a cutting blade 10 disposed between the two pin shanks 54 is not retained therebetween. On the other hand, the distance between the two pin heads 56 is a distance substantially the same as the distance between the pair of notches 51, so that a cutting blade 10 disposed between the two pin heads 56 is firmly retained therebetween.

As shown in FIGS. 7 and 8, the cutting saw 14 further comprises a mechanism 58 for moving both of the pins 52 together from a first pin position wherein the pins 52 can retain a cutting blade 10 disposed between the pins 52 and a second pin position wherein the pins 52 do not retain a cutting blade 10 disposed between the pins 52. The mechanism 58 illustrated in FIGS. 7 and 8 consists of a push button 60 which presses against a t-bar 62. The t-bar 62, in turn, pushes against the base 64 of each of the two pin shanks 54. Thus, when the push button 60 is pressed upwards, both pins 52 are simultaneously pushed upwards. As shown in FIG. 8, the two pins 52 are in a first pin position wherein a cutting blade 10 is retained between the two pin heads 56. After the push button 60 is pressed, the two pins 52 are elevated to a second pin position wherein the cutting blade 10 is directly between the two pin shanks 54. Because the distance between the pin shanks 54 is greater than the distance between the pin heads 56, the cutting blade 10 is no longer firmly attached to the oscillatory saw 14.

Having thus described the invention, it should be apparent that numerous structural modifications and adaptations may be resorted to without departing from the scope and fair meaning of the instant invention as set forth hereinabove and as described hereinbelow by the claims.

What is claimed is:

1. An oscillatory cutting saw useful for surgical penetration of bone comprising:
   (a) an oscillatory power tool having a blade retention device;
   (b) a cutting blade attached to the oscillatory cutting saw, said blade comprising:
      (i) a central cutting blade shank having a longitudinal axis;
      (ii) a distal end having a plurality of cutting teeth disposed substantially on a tangent perpendicular to the longitudinal axis of the cutting blade shank; and (iii) a proximal end having a plurality of spaced-apart attachment elements, each of said attachment elements being capable of cooperating with the blade retention device so as to firmly attach the blade to the oscillatory cutting saw;

whereby the attachment of the blade to the oscillatory cutting saw by one of the attachment elements results in a distance between the cutting teeth and the blade retention device which is different from the distance between the cutting teeth and the blade retention device resulting from the attachment of the blade to the oscillatory cutting saw by a different attachment element.

2. The oscillatory cutting saw of claim 1 wherein the blade retention device comprises a pair of spaced-apart parallel pins shaped and dimensioned to receive and retain a cutting blade which is disposed between the pins.

3. The oscillatory cutting saw of claim 2 wherein the pins each have a pin shank and a pin head and wherein the pin heads are shaped and dimensioned to receive and retain a cutting blade which is disposed between the pin heads and the pin shanks are shaped and dimensioned to not retain a cutting blade which is disposed between the pin shanks.

4. The oscillatory cutting saw of claim 2 further comprising a mechanism to move both pins together from a first pin position wherein the pins retain a cutting blade disposed between the pins and a second pin position wherein the pins do not retain a cutting blade disposed between the pins.

5. The oscillatory cutting saw of claim 4 wherein the pins each have a pin shank and a pin head and wherein the pin heads are shaped and dimensioned to receive and retain a cutting blade which is disposed between the pin heads, and the pin shanks are shaped and dimensioned to not retain a cutting blade which is disposed between the pin shanks, and wherein the mechanism comprises a push button which, when pushed, impinges upon both pin shanks to move both pins simultaneously from the first pin position to the second pin position.

6. The oscillatory cutting saw of claim 1 wherein the attachment elements are pairs of opposed notches.

7. The oscillatory cutting saw of claim 1 wherein the teeth are substantially shaped as right triangles.

8. A cutting blade for use with an oscillatory cutting saw having a blade retention device such as an oscillatory cutting saw used to surgically cut bone, the cutting blade comprising:

(a) a central cutting blade shank having a longitudinal axis;

(b) a distal end having a plurality of cutting teeth disposed substantially on a tangent perpendicular to the longitudinal axis of the cutting blade shank; and (c) a proximal end having a plurality of spaced-apart attachment elements, each of said attachment elements being capable of cooperating with the blade retention device so as to firmly attach the blade to the oscillatory cutting saw;

whereby the attachment of the blade to a oscillatory cutting saw by one of the attachment elements results in a distance between the cutting teeth and the blade retention device which is different from the distance between the cutting teeth and the blade retention device resulting from the attachment to the oscillatory cutting saw by a different attachment element.

9. The cutting blade of claim 8 wherein the teeth are substantially shaped as right triangles.

10. The cutting blade of claim 8 wherein the hypotenuse of each tooth faces away from the center of the distal end.

11. The cutting blade of claim 8 wherein the hypotenuse of each tooth faces towards the center of the distal end.

12. The cutting blade of claim 8 wherein the number of teeth is between about 6 and about 16.

13. The cutting blade of claim 8 wherein the length of the cutting blade is between about 6 cm and about 18 cm, the width of the cutting blade is between about 1 cm and about 4 cm, and the thickness of the cutting blade is between about 0.6 mm and about 2 mm.

14. The cutting blade of claim 8 wherein the attachment elements are pairs of opposed notches.

15. The cutting blade of claim 14 wherein the pairs of opposed notches are spaced-apart by between about 1 cm and about 5 cm.

16. A cutting blade for use with an oscillatory cutting saw having a blade retention device such as an oscillatory cutting saw used to surgically cut bone, the cutting blade comprising:

(a) a central cutting blade shank having a longitudinal axis;

(b) a distal end having between about 6 and about 16 teeth disposed substantially on a tangent perpendicular to the longitudinal axis of the cutting blade shank, each tooth being shaped substantially as a right triangle; and (c) a proximal end having a plurality of pairs of opposed notches, each of the notches being capable of cooperating with the blade retention device as to firmly attached the blade to the oscillatory cutting saw;

wherein the attachment of the blade to an oscillatory cutting saw by a pair of the opposed notches results in a distance between the cutting teeth and the blade retention device which is different from the distance between the cutting teeth and the blade retention devices which results from the attachment to the oscillatory cutting saw by a different pair of opposed notches.

17. The cutting blade of claim 16 wherein the hypotenuse of each tooth faces away from the center of the distal end.

18. The cutting blade of claim 16 wherein the hypotenuse of each tooth faces towards the center of the distal end.

19. The cutting blade of claim 16 wherein the length of the cutting blade is between about 6 cm and about 18 cm, the width of the cutting blade is between about 1 cm and about 4 cm, and the thickness of the cutting blade is between about 0.6 mm and about 2 mm.

20. The cutting blade of claim 16 wherein the pairs of opposed notches are spaced-apart by between about 1 cm and about 5 cm.

* * * * *